United States Patent [19]

Lowell

[11] Patent Number: 5,895,841
[45] Date of Patent: Apr. 20, 1999

[54] METHOD AND APPARATUS FOR PERFORMING ADSORPTION AND DESORPTION ANALYSIS OF SAMPLES

[75] Inventor: Seymour Lowell, Lake Worth, Fla.

[73] Assignee: Quantachrome Corporation, Boynton Beach, Fla.

[21] Appl. No.: 08/688,032

[22] Filed: Jul. 26, 1996

[51] Int. Cl.⁶ .................................................. G01N 15/08
[52] U.S. Cl. ..................................... 73/38; 73/865.5
[58] Field of Search .................. 73/38, 37.5, 865.5

[56] References Cited

U.S. PATENT DOCUMENTS

| | | | |
|---|---|---|---|
| 3,059,478 | 10/1962 | Coggeshall et al. | 73/38 |
| 3,299,713 | 1/1967 | Haul et al. | 73/865.5 |
| 3,349,625 | 10/1967 | Benusa et al. | 73/865.5 |
| 3,555,912 | 1/1971 | Lowell | 73/432 |
| 4,566,326 | 1/1986 | Lowell | 73/432 |
| 5,133,219 | 7/1992 | Camp | 73/865.5 |
| 5,360,743 | 11/1994 | Lowell | 436/5 |

*Primary Examiner*—Michael Brock
*Attorney, Agent, or Firm*—Robert M. Schwartz; Edward I. Mates

[57] ABSTRACT

An adsorption and desorption analyzer for performing analyses on samples comprises a manifold for selectively storing one or two gases or vapors having different critical temperatures, at least two cells constructed and arranged to store a sample for analysis, a supply line having an isolation valve connecting each cell to the manifold, an absolute pressure transducer for monitoring the pressure in the manifold, vacuum means, a microprocessor for controlling the operation of the isolation valves and the application of gas or vapor or vacuum to the manifold and a coupling line having a differential pressure transducer having a smaller range than the range of the absolute pressure transducer, enables an operator to determine data points for characteristics of the samples under study more precisely and more rapidly than is possible using an analyzer having an identical absolute pressure transducer for each cell to determine the characteristics of the samples stored in the cells. The analyzer is also constructed and arranged to determine the characteristics of additional samples in addition to the first pair of samples compared.

17 Claims, 2 Drawing Sheets 5,895,841

1

METHOD AND APPARATUS FOR PERFORMING ADSORPTION AND DESORPTION ANALYSIS OF SAMPLES

BACKGROUND OF THE INVENTION

1. Field of the Invention

The present invention relates generally to measurement techniques for performing adsorption and desorption gas analyses on materials, and more particularly to an improved technique and apparatus for simultaneously and independently performing gas adsorption and desorption measurements on a plurality of different samples, such as powder or pellet samples, for example.

Dozens of patents have been issued for method and apparatus for measuring gas adsorption of samples The prior art most pertinent to the present invention involves methods and apparatus which use absolute pressure transducers in the measurement of adsorption on a plurality of samples simultaneously, and methods and apparatus which use differential pressure transducers for purposes different than those of the present invention.

A great variety of applications in modern technology require accurate information concerning the microstructure of materials such as powders which are widely used, for example, as catalysts or in the production of paint, cement, and the like. This information includes the porosity and surface areas of the powder material and the distribution of pore volume in the various sized pores.

One conventional manner of performing such measurements, which is disclosed, for example, in U.S. Pat. No. 3,555,912 to Lowell (Lowell '912), involves the preparation of adsorption and desorption isotherms of the material in which volume is plotted against the equilibrium relative pressure of the gas (typically nitrogen) adsorbed or desorbed on the surface of the material. To prepare such isotherms, the quantity of the gas adsorbed onto the solid surface or desorbed from the solid surface is measured at various specified pressures at a specific temperature. The conventional gas adsorption and desorption processes are, however, relatively slow, often requiring hours or sometimes even days to acquire the necessary data to accurately characterize the porosity and surface area of the material.

Many types of vacuum-volumetric apparatus and systems have been developed for performing adsorption and desorption measurements on samples. Many of these adsorption and desorption measurement systems have certain essential features. These include a non-adsorbable gas (e.g. helium) for calibrating the volume of the cell containing the sample, (except for the so called NOVA system manufactured by Quantachrome Corporation of Boynton Beach, Fla.). U.S. Pat. No. 5,360,743 to Lowell, which avoids the need for such calibration and another technique to be described later) and an adsorbate gas (e.g. nitrogen) for performing the adsorption or desorption analysis. The non-adsorbable gas is critical in these systems for calibrating the volume of the sample cell with the sample material present.

The prior art has speeded the production of analytical data to some extent. U.S. Pat. No. 4,566,326 to Lowell (Lowell '326) provides an analyzer unit capable of concurrently and independently obtaining data for a plurality of powder samples in a single measuring instrument.

It is the main object of the aforesaid patented invention to provide an analyzer unit which is capable of acquiring data on several samples substantially simultaneously and in which the data derived for a plurality of samples can be stored and presented in any of a number of different forms for each of the samples. To these ends, the automatic measurement units of the invention described and included in the aforesaid Lowell '326 patent includes a common manifold in respective fluid communication through a plurality of isolation valves with a corresponding plurality of sample cells, and absolute pressure transducers are provided to measure the manifold pressure, and a plurality of absolute pressure transducers are respectively coupled to the sample cells (a separate absolute pressure transducer for each sample cell) to provide measurement of the respective pressures in the sample cells.

The Lowell '326 invention operates automatically under the control of a microprocessor, which receives and processes information from the several pressure transducers and controls the operation of the isolation valves. This microprocessor measures current cell pressure, manifold temperature and manifold pressure. When the manifold and cell are connected through an opened isolation valve, a pressure in the combined volume results. This latter pressure is used to calculate a specified relative pressure. The manifold is then pressurized to the calculated value with nitrogen gas, and the cell isolation valve is opened to allow a volume of nitrogen to be admitted (or removed) into (or from) one of the sample cells which contain the solid adsorbent sample to be analyzed. The isolation valve is then closed. As adsorption (or desorption) of the gas occurs in the sample, the pressure in the sample cell as measured periodically by the cell pressure transducer varies until an equilibrium pressure or relative pressure is attained. Relative pressure is defined as the ratio of the equilibrium pressure (P) to the saturated vapor pressure ($P_o$), expressed as $P/P_o$. The quantity of the gas adsorbed (or desorbed) at the equilibrium pressure is the difference between the amount of gas admitted (or removed) and the amount required to fill the space around the adsorbent (void space) which was previously determined with non-adsorbable helium gas.

This process is repeated for different volumes and relative pressures until a preselected number of data points have been produced for the sample. At one of several stages in the analysis sequence of a given sample cell at which an interval or delay is required, the processing of analysis is shifted for that period to another of the sample cells according to a priority programmed into the microprocessor. This process of shifting the operations between the sample cells on a priority basis continues in a sequence determined to achieve optimum analysis, until the required pressure-volume data points for all of the samples under analysis have been obtained.

Other pertinent prior publications relevant to this invention in addition to the aforesaid Lowell '326 patent include a book entitled "Adsorption, Surface Area and Porosity" by S. J. Gregg and K. S. W. Sing, published in 1967 by Academic Press, London and New York (particularly pages 324 to 326); a "Strohlein AREA-Meter" brochure and U.S. Pat. No. 5,133,219 to Camp (Camp '219).

As will be explained later, these latter publications incorporate a differential pressure transducer between a sample cell and a comparison cell. In the Strohlein AREA-Meter and Camp '219, the comparison cell is used as a reference only and is not used with a sample in the cell. The sole purpose of the differential gauge and the reference cell is to determine the amount of gas not adsorbed on the sample surface in the sample cell. These publications differ from the present invention in that results obtained in the prior art are not acquired as rapidly as are obtainable with the present invention. It is believed that the prior art fails to obtain the rapid obtention of data possible with the present invention because the prior art measures only one sample cell at a time.

U.S. Pat. No. 5,360,743 to Lowell (Lowell '743) provides an improved apparatus and method for measuring the void volume, and the adsorption of the sample cell walls, and correcting for non-ideal gas behavior by using only the adsorbate gas. This Lowell invention effectively overcomes the aforementioned difficulties and longstanding problems inherent in surface area and pore volume measurements. These problems have been solved in a simple, convenient, and highly effective way by which to increase the accuracy of the measurement and to decrease the time consumed in performing the measurements.

Despite the improvements developed in the technology as evidenced by the patents described hereinbefore, there still remains room for further improvements that enable the art to obtain the requisite data even more rapidly using modified apparatus that is less costly in that the present apparatus eliminates an expensive component previously required in the prior art as will be described hereafter.

SUMMARY OF THE INVENTION

The present invention represents further improvements over what is disclosed and claimed in the aforesaid Lowell '326 patent. The present apparatus includes an attachment of a plurality of cells to a manifold, a supply line unique for each sample cell communicating its associated sample cell to the manifold, an isolation valve in each of said supply lines between the manifold and its associated sample cells, and a differential pressure transducer between a related one of said supply lines to another of said supply lines and located on the cell side of said isolation valves. The differential pressure transducer is constructed and arranged relative to said supply lines in such a manner that the need for an individual absolute pressure transducer for each of said supply lines is no longer necessary as is required in the prior art. This latter feature constitutes one of the cost saving features of the present invention. As used herein, the terms "transducer" or gauge and/or gauge can be used interchangeably, and "gauge" can mean transducer and, vice versa, transducer can mean gauge. Additionally, the term gas can also mean vapor and can be used interchangeably.

The apparatus according to this invention reduces the number of pressure transducers required from a number of absolute pressure transducers equal to the number of sample cells in the analyzer plus those attached to the manifold to at least one single absolute pressure transducer attached to the manifold and a number of differential pressure transducers that is one less than the number of sample cells. The term "absolute pressure transducer" is not necessarily limited to one transducer but may be used for any plurality of absolute pressure transducers required to cover the range of pressures being measured, such as three absolute pressure transducers, the first having a scale from 0 to 1,000 mm of mercury, the second having a scale from 0 to 10 mm of mercury and the third having a scale from 0 to 1 mm of mercury, for example.

A differential pressure transducer that is included in the present invention has a smaller range centered about zero compared to a wider range indicated on an absolute pressure transducer.

Each supply line is provided with an isolation valve. Each supply line has a cell at its distal end remote from the manifold and its isolation valve is located between the manifold and the cell at its distal end. The coupling line interconnects a pair of supply lines between the isolation valves on one hand and the cells on the other hand. Each cell takes a turn serving as a reference cell when the other cell serves as a sample cell. When the supply line for one cell has its isolation valve open while the isolation valve for the other supply line is closed, the one cell for the first named supply line is considered the reference cell and the cell for the other supply line is considered to be the sample cell. The reference cell has the same pressure as the manifolds while the sample cell has a pressure that differs from that of the one cell by the value indicated by the differential pressure transducer. When the isolation valve conditions are reversed, the one cell that was initially the reference cell becomes the sample cell and vice versa.

Pairing the supply line to the reference cell with another supply line for the sample cell and programming the opening and closing of the isolation valves as described hereinafter determines a reference pressure for any chosen reference cell. Any reference cell chosen is paired to each other sample cell in turn while any remaining sample cells are isolated from the pair of sample cells that are coupled and from the manifold until the differential pressure transducer indicates the pressure differential between the sample cell and the reference cell of the pair being compared.

One or the other of any pair of cells comprising a reference cell and a sample cell being compared is dosed as needed until dynamic equilibrium is established within each cell. The pressure in the reference cell is determined by the pressure in the sample cell plus or minus the differential pressure transducer reading. A computer decides which reference cell and which sample cell is to be included in each pair of cells to be compared in turn.

After establishing a pressure reading for the first pair of cells comprising a sample cell and a reference cell, the computer chooses another cell to be compared and repeats the comparison process for a second pair of sample and reference cells that includes one of the first pair of cells selected to be the reference cell and another sample cell that has not yet been compared. This pairing and comparing is repeated until every other sample cell has been paired and compared with a cell chosen to be a reference cell at a given pressure.

The aforesaid process is repeated at several different pressures for several comparison pairs of each sample cell and said reference cell until enough data points are established on a data chart to satisfy a customer's needs. The manifold temperature, pressure and calibrated volume is fed to a computer to calculate the quantity of gas in the manifold in order to calculate the volume of gas introduced into each cell.

Accuracy is enhanced because a differential pressure transducer having a range that reads, for example, from −10 mm of mercury pressure differential to +10 mm of mercury pressure, is much more accurate than an absolute pressure transducer having a range that reads from 0 to actual environmental conditions.

To illustrate the benefits of this invention, if we assume that pressure transducers having an accuracy of 1% are available at a reasonable price, an absolute pressure transducer having a scale of 0 to 1000 mm (i.e., a 1000 mm range) in pressure readings gives a resolution of 10 mm pressure at 1% accuracy and would require an accuracy of 0.01% (or one hundred times the precision) to obtain a resolution of 0.1 mm pressure. An absolute pressure transducer or gauge of such precise accuracy (0/01%) is much more expensive than one constructed and arranged to provide 1% accuracy. On the other hands a differential pressure transducer or gauge having a scale of −5 mm to +5 mm (i.e., a 10-mm range)

needs only a 1% accuracy to obtain a resolution of 0.1 mm pressure and one having a scale of −10 mm to +10 mm (i.e., a 20-mm range) in pressure readings needs an accuracy of 0.5% to obtain a resolution of 0.1 mm pressure. An absolute pressure transducer or gauge having a resolution of 0.1 mm pressure and a scale of 0 to 1000 mm in pressure readings requires an accuracy of 0.01% or must be fifty times more precise than a differential pressure transducer or gauge having a 20-mm range in pressure readings.

The method and apparatus of the present invention will be better understood by reference to the following detailed discussion of specific embodiments and the attached figures which illustrate and exemplify such embodiments.

DESCRIPTION OF THE DRAWINGS

Specific embodiments of the present invention will be described with reference to the following drawings wherein.

DESCRIPTION OF THE PREFERRED EMBODIMENT

Figure 1:
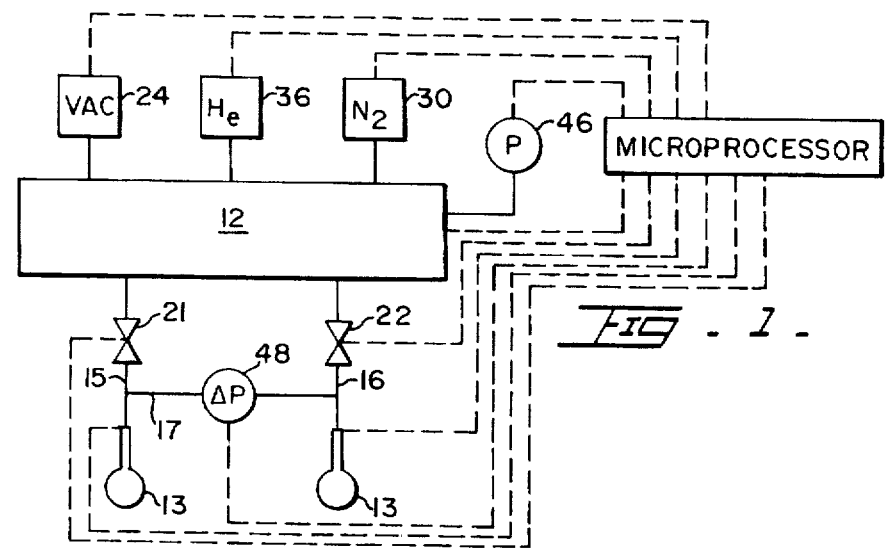
FIG. 1 is a schematic diagram of the apparatus of the present invention that comprises a manifold coupled by a valved supply line to a single sample cell and another valved supply line to another sample cell, either one of which can be selected as a reference cell.

The multi-sample surface analyzer of the invention, as shown in FIG. 1, includes a manifold 12 from which a plurality (here two) of supply lines 15 and 16 whose lower ends terminate in two cells 13, one designated as a reference cell and the other designated as a sample cell. Positioned below cells 13 are at least one or more flasks (not shown) which contain a coolant required to cause the adsorbing gas to adhere to the sample surface. The latter are supported on a lower shelf (not shown) and are each movable vertically between a lower recessed position below its associated cell and an upper raised position wherein a liquid stored in a flask at a low temperature envelops the cell in a manner conventional to this technology.

The analyzer unit of FIG. 1 is capable of performing concurrent and independent volumetric adsorption and desorption analyses on a plurality of solid powder samples placed within each cell 13. To this end, as shown in FIG. 1, the sample cells 13 are coupled to the manifold 12 by means of a plurality of supply lines 15 and 16 provided with respective isolation valves 21 and 22. Also coupled to the manifold 12 are a vacuum source 24 by means of vacuum control valve means; a source of a gas or vapor having a relatively high critical temperature such as nitrogen 30 coupled through nitrogen control valve means; and a source of a gas or vapor having a relatively low critical temperature such as helium 36 coupled through helium control valve means.

An absolute pressure transducer or gauge 46 is coupled to the manifold 12 to monitor the absolute pressure in manifold 12 and that of either cell 13 that serves as a reference cell when its associated valve 21 is open and the other valve 22 associated with the other cell 13 is closed. When valve 22 associated with the other cell 13 is open and valve 21 is closed, the other cell serves as the reference cell. A differential pressure transducer or gauge 48 is connected to a coupling line 17 interconnecting supply lines 15 and 16 distal to their respective isolation valves 21 and 22. The differential pressure transducer or gauge 48 is constructed and arranged to cooperate with absolute pressure transducer or gauge 46. To measure absolute pressure in the left cell 13 (as seen in FIG. 1), isolation valve 21 is open and isolation valve 22 is closed. To measure absolute pressure in the right cell 13, isolation valve 22 is open and isolation valve 21 is closed.

To obtain an absolute pressure reading on the cell not opened to the manifold, the differential pressure reading is added to or subtracted from the absolute pressure transducer or gauge reading for the cell open to the manifold. This will be made any time the differential pressure transducer or gauge reading is on scale and not changing at a faster rate of change than the maximum rate of change acceptable by the user. This means the equilibrium has been obtained and data can be taken. The increased accuracy associated with a smaller range differential pressure transducer or gauge improves the ability of the instrument to measure equilibrium pressure at a lower cost.

There is need for only one absolute pressure transducer or gauge 46 in combination with either supply line 15 and 16 compared to a plurality of absolute pressure transducers or gauges required in the prior art. Instead, the present invention provides a single absolute pressure transducer or gauge 46 in cooperation with a single differential pressure transducer or gauge 48 (in the FIG. 1 embodiment) to perform the functions that required a plurality of absolute pressure transducers or gauges in the prior art.

Coupling line 17 is provided with a sensitive differential pressure transducer or gauge 48 having a differential scale over a narrow pressure range, say from −5 to +5 mm of mercury, for example, whereas absolute pressure transducer or gauge 46 for manifold 12 indicates a large pressure range from zero to an elevated pressure that may be greater than standard atmospheric pressure (e.g., 1000 mm). Therefore, during a pressure comparison test when differential pressure transducer or gauge 48 in coupling line 17 indicates an imbalance in pressure between left and right cells 13, a redose is applied to the cell 13 having a lower pressure to reduce the pressure imbalance between the cells. If desorption data is being acquired, an amount of gas can be removed from the cell. The instrument will redose (or remove gas) if the differential pressure gauge is off scale or if the pressure reading on the differential pressure gauge indicates the lower target pressure has not been achieved. A relatively easily readable change of differential pressure is detectable on the differential pressure transducer or gauge 48 which may not be observable on an absolute pressure transducer or gauge covering a wide range as known in the prior art.

A programmed microprocessor 50 is electrically connected directly or through a bus to receive and transmit measurement and control signals from the transducers or gauges 46 and 48 and to the control valve means for vacuum source 24, nitrogen source 30 and helium source 36, all coupled to manifold 12. Additionally, the microprocessor controls the valves in the supply lines and all the functions of the cells.

In brief, the analyzer unit of the invention, as illustrated in FIG. 1, operates under the control of the microprocessor in accordance with the program described hereinafter to measure the quantity of gas adsorbed onto or desorbed from a solid surface of the sample material within the pair of cells under study at a present equilibrium pressure by the static volumetric method. The data are obtained by admitting or removing a known quantity of adsorbate gas (here nitrogen) from the manifold 12 into or out of one of the cells 13 containing the solid adsorbent maintained at a constant temperature below the critical temperature of the adsorbate. As adsorption or desorption occurs, the pressure in the cell 13 undergoing dosing changes until an equilibrium pressure is established. The quantity of gas adsorbed or desorbed at the equilibrium pressure is the difference between the amount of gas admitted or removed and the amount required to fill the space around the adsorbent (void space).

This volume-pressure data can be processed to produce at a monitor, at the option of the unit operator, the following well known outputs: a BET surface area, a single-point BET area, a Langmuir surface area plot, adsorption and/or desorption isotherms, pore size and surface area distributions, micropore volume and surface area using t-plots and total pore volume and average pore radius. Further it can reduce the data according to density functional theory and many other theories associated with gas adsorption. For additional information concerning the B.E.T. (Brunauer, Emmett and Teller) plot and the Langmuir surface area plot, see *Introduction to Powder Surface Area*, by Seymour Lowell, Chapman and Hall, 3rd Edition, 1991. Significantly, the analyzer unit of the invention is capable of performing such analyses substantially simultaneously and independently on a plurality of powder samples to produce this data in the manner described subsequently It will be understood that while the steps described for analyzing the samples in a pair of sample cells, processing is actually performed on only one sample at any instant of time, at certain intervals in each sample processing sequence. Processing of all or part of a measurement sequence can also be performed on one or more additional samples. Accordingly, during a given interval, all or part of a sample analysis can be carried out on as many samples as are contained in the sample cells in the analyzer units of FIGS. 2 and 3. While six samples are shown in FIG. 3 and cited in the specification, it is understood that any apparatus containing any number of cells to be compared is encompassed by this invention.

Before reading is begun on any sample, a leak test is performed on the system and on the sample cells. It is necessary to calibrate the absolute pressure transducer or gauge to a zero pressure reading The following steps are to be taken:

1. Pump down the manifold until pressure is at a minimum and the pressure reading is taken as the zero reading of the absolute pressure transducer,
2. The sample cells are evacuated, and
3. When the system gets to zero pressure or within a certain tolerance of zero pressure, close valves and determine if there is a leak by monitoring the differential pressure gauge, or alternatively, the valve to any one cell can be opened and the pressure monitored on the absolute pressure transducer. An advantage of using the differential pressure gauge transducer or gauge is its own higher sensitivity in a smaller volume to detect any leaks; however, as shown in the FIG. 1 embodiment, when two cells are being compared, this leak test will be in error, only if both cells have identical leakage rates. However, it is most improbable for both cells to leak at the same leakage rate.

Thus, if at the end of the leak test delay, it is determined that the sample cell has not passed the leak test, and that there is a leak in the system somewhere in the sample cell or in the piping between that cell and the manifold, the cell is backfilled with helium and the operator is informed that a leak has been detected. At this point, processing at that cell is terminated.

From the prior art, it is well known that it is necessary to determine the volume of the manifold and perform a void volume measurement which is described in the Lowell '326 patent, which is incorporated herein by reference.

To build an isotherm on two samples, dose either of the two cells to the first requested target pressure, with a first valve to a first cell open and a second valve to a second cell closed. When the target pressure is reached in the first cell, the first valve is closed and the second valve is opened to allow gas (gas pressure having been previously set in the manifold) to flow into the second cell (the target pressure for this second cell to be the same as the first cell target pressure). If necessary, several doses may be added to a cell to achieve the target pressure, which is true for any data point.

If the differential pressure transducer or gauge is drifting, this indicates one or the other cell has failed to reach equilibrium and adsorption is still occurring.

If at the end of a predetermined period of time, the differential pressure transducer or gauge stops drifting, indicating equilibrium has been achieved, then the pressure in the second cell can be read from the absolute pressure transducer or gauge and the pressure in the first cell is that pressure plus or minus the reading from the differential pressure transducer or gauge.

If the differential pressure transducer or gauge, while waiting for equilibrium to be established, drifts off scale, indicating adsorption has occurred in one of the cells, dropping the pressure when compared to the other cell out of the range of the differential pressure transducer or gauge, then that cell with the low pressure will be dosed again to the target pressure. Continued adsorption indicating equilibrium has not been reached will produce a slower drop in pressure in the cell open to the manifold compared to the faster rate of pressure drop in the cell having its valve closed, because the manifold can continue to supply gas to that cell out of a much greater volume than is available to the cell with the valve closed whose pressure will drop much more rapidly for an equal amount of adsorption. The system continues to dose to the target pressure. When the target pressure is reached and the readings have been transferred to the microprocessor, then repeat to the next target pressure data point.

In order to achieve the next target pressure, both valves are closed, the manifold pressure is increased and again either cell valve can be opened to build pressure in its corresponding cell. Having achieved the target pressure in the first cell, the first valve is closed and the manifold pressure is increased to dose the second cell. When equilibrium is reached, the pressure in the second cell is read from the absolute pressure transducer or gauge and the other cell pressure is equal to the pressure of the absolute pressure transducer or gauge plus or minus the pressure reading of the differential pressure transducer or gauge. This process is continued until all data points are achieved on the adsorption isotherm In order to obtain data points on the desorption isotherm, the process described above is reversed, namely a first cell is chosen such that when the manifold pressure is reduced that cell's valve is opened, causing gas to flow out of the first cell into the manifold, causing gas to desorb. When target pressure is reached, the first valve on the first cell is closed and the same procedure is used to cause desorption on the sample in the second cell. When the target pressure of the second cell is reached, the second valve to the manifold remains open and the equilibrium pressure when equilibrium is reached is read on the absolute pressure transducer or gauge while the equilibrium pressure in the first cell will read as absolute pressure transducer or gauge plus or minus the pressure reading of the differential pressure transducer or gauge. As described above for adsorption, this process is repeated until all desorption data points are obtained.

For multiple cells (more than two cells) the first cell is dosed to the target pressure and the first valve is closed, each subsequent cell, Cn is dosed to target pressure and the corresponding valve Vn for cell Cn is closed until the last cell is dosed. If the last cell to be dosed is the nth cell, its pressure is read on the absolute pressure transducer or gauge and the pressure of the previous cell. Cn-1 is the pressure reading on the absolute pressure transducer or gauge plus or minus the pressure reading of the differential pressure transducer or gauge. The pressure of the second from last cell, Cn-2 is the just obtained pressure reading above, plus or minus the reading of the differential pressure transducer or gauge between the Cn-1 cell and Cn-2 cell, and the Cn-3 cell pressure is the above pressure reading plus or minus the reading of the differential pressure transducer or gauge between the Cn-2 cell and Cn-3 cell. These readings are continued for as many cells as designed in the system In the system with more than two cells, the sequence of reaching target pressure among cells is to dose and bring to target pressure and equilibrium pressure those cells closest to the cell which had the last reading on the absolute pressure transducer first. This minimizes errors as a result of the manifold and supply line volumes to the cell whose pressure is being read by the absolute pressure transducer or gauge.

The apparatus shown schematically in FIG. 1 is used for analysis in the following manner. The sample is first prepared for analysis by applying samples to cells 13 and designating one of said cells as a reference cell, and the other of said cells as a sample cell, and evacuating the entire system. The volume of the manifold used to perform the method of this invention would be previously calibrated using the method described in the aforesaid Lowell '326 patent, the details of which are incorporated herein by reference.

After the analyzer has been evacuated, and all valves closed, the following steps are performed:

(Step I)—Increase the pressure in manifold 12 to a pressure sufficient to deliver a dose of gas that will achieve a pressure requested in the left cell 13 when valve 21 is opened as described in the Lowell '326 patent (Step II)—Open valve 21 and allow time for the gas to transfer. Close valve 21.

(Step III)—Calculate the volume of gas added to the left cell 13 by determining the change in pressure in the manifold 12 reported by absolute pressure transducer or gauge 46 before and after the gas transfer.

(Step IV)—Make a dose for the right cell after opening valve 22. However, do not close valve 22 after dosing.

(Step V)—monitor the pressure in the right cell 13 with absolute manifold transducer or gauge 46 (valve 22 is open). The pressure in left cell 13 is derived by applying the differential pressure indicated in differential pressure transducer or gauge 48 to the pressure indicated by absolute pressure transducer or gauge 46 for the right cell 13.

(Step VI)—Wait for the left and right cells 13 to equilibrate. If one of the two cells 13 comes to a pressure outside of the range of the differential pressure transducer or gauge, or outside the tolerance or target pressure desired, continue as follows:

A. If left cell 13 indicates a pressure below the target pressure, with valve 22 open, adjust the pressure in manifold 12 to obtain a pressure in the left cell 13 close to the target pressure.

1. Close valve 22 and calculate the volume of gas to be transferred.
2. Build up the pressure in manifold 12 to redose the left cell 13.
3. Transfer the gas by opening valve 21.
4. Monitor the pressure in the left cell 13 with absolute manifold transducer or gauge 46. The pressure in right cell 13 is derived by applying the differential pressure indicated in differential pressure transducer or gauge 48 to the pressure indicated by absolute pressure transducer or gauge 46 for the left cell 13.

B. If right cell 13 indicates a cell pressure that falls outside the tolerance band, right valve 22 remains open:

1. Close valve 22, calculate the volume of gas to be transferred.
2. Build pressure in manifold 12 to redose the right cell 13.
3. Transfer the gas by opening valve 22.
4. Monitor the pressure in the right cell 13 with absolute manifold transducer or gauge 46. The pressure in left cell 13 is derived by applying the differential pressure indicated in differential pressure transducer or gauge 48 to the pressure indicated by absolute pressure transducer or gauge 46 for the right cell 13.

C. When both cells come to equilibrium at the requested pressure:

1. The volume adsorbed by the sample may be calculated as the sum total volume of gas added to the sample cell less the volume of gas required to fill the void volume at the equilibrium pressure.
2. Store the data.
3. Select the next requested point (if there is one) and return to Step I.
5. Otherwise the analysis is complete.

Figure 4:
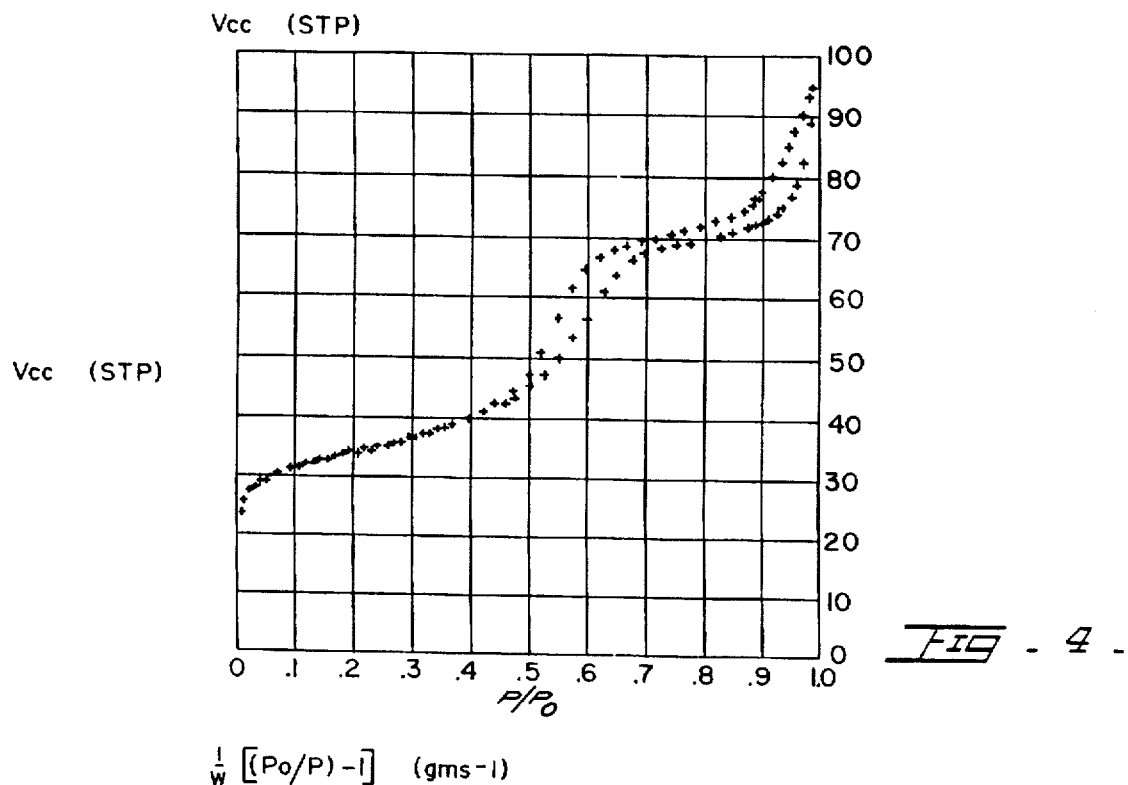
FIG. 4 is a typical adsorption-desorption isotherm that can be produced from the data obtained by the analyzer of the invention
Figure 5:
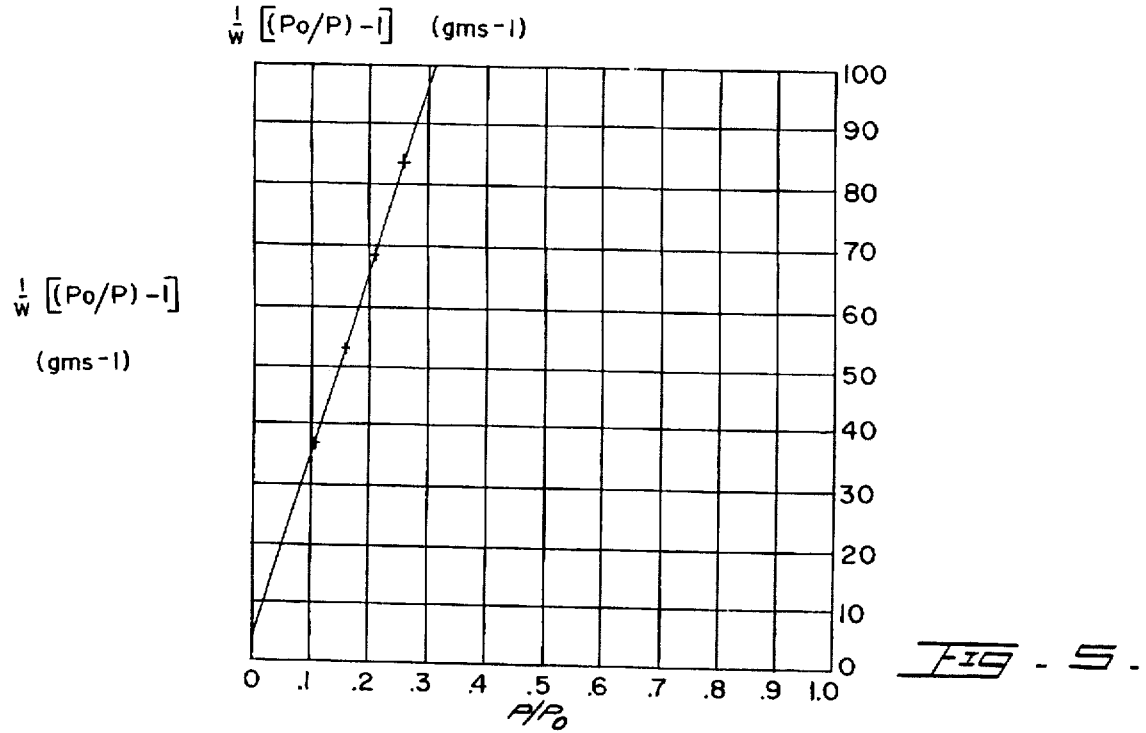
FIG. 5 is a typical B.E.T. curve that can be produced from the data obtained by the analyzer of the invention

The process just described is repeated for different volumes and relative pressures as described previously to develop a plurality of data points for the sample. FIGS. 4 and 5 illustrate typical data charts obtained from the process just described. FIG. 4 shows a typical adsorption-desorption isotherm, and FIG. 5 shows a typical B. E. T. curve that can be obtained from the analyzer of this invention.

The FIG. 1 embodiment is able to develop the data desired for two cells substantially simultaneously. The FIG. 2 embodiment is constructed and arranged to perform a similar treatment to determine the data for three samples from substantially simultaneously comparing two different pairs of samples from the three samples in the three cells of the FIG. 3 embodiment. The FIG. 3 embodiment is capable of developing data charts for six samples by substantially simultaneously comparing five different pairs that include all of the six samples tested by the FIG. 3 embodiment. After studying the descriptions of the other two embodiments, the reader should be able to understand that the embodiments described herein are exemplary only and that analyzers capable of analyzing any number of samples substantially simultaneously can be inferred from what is disclosed herein.

Figure 2:
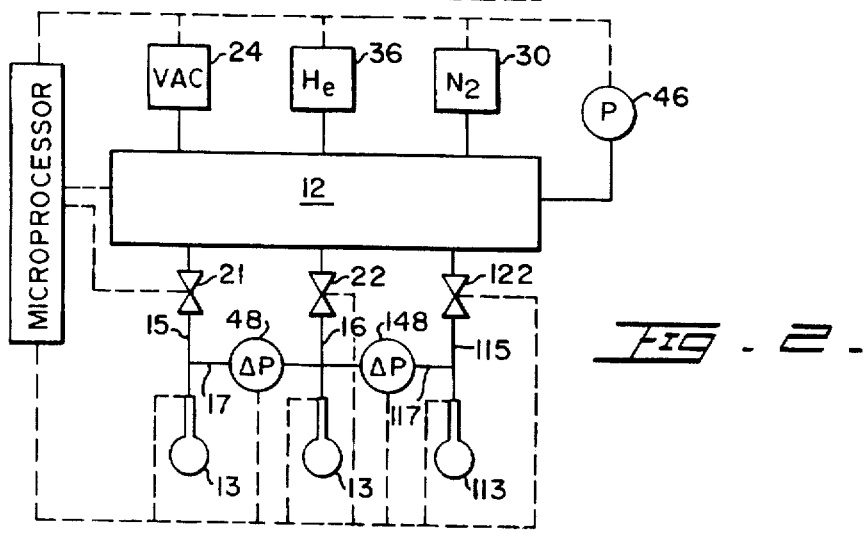
FIG. 2 is a schematic diagram of another embodiment of apparatus conforming to this invention that comprises a set of three sample cells coupled to a manifold through separate valved supply lines, any one of which cells can be selected to be a reference cell.
Figure 3:
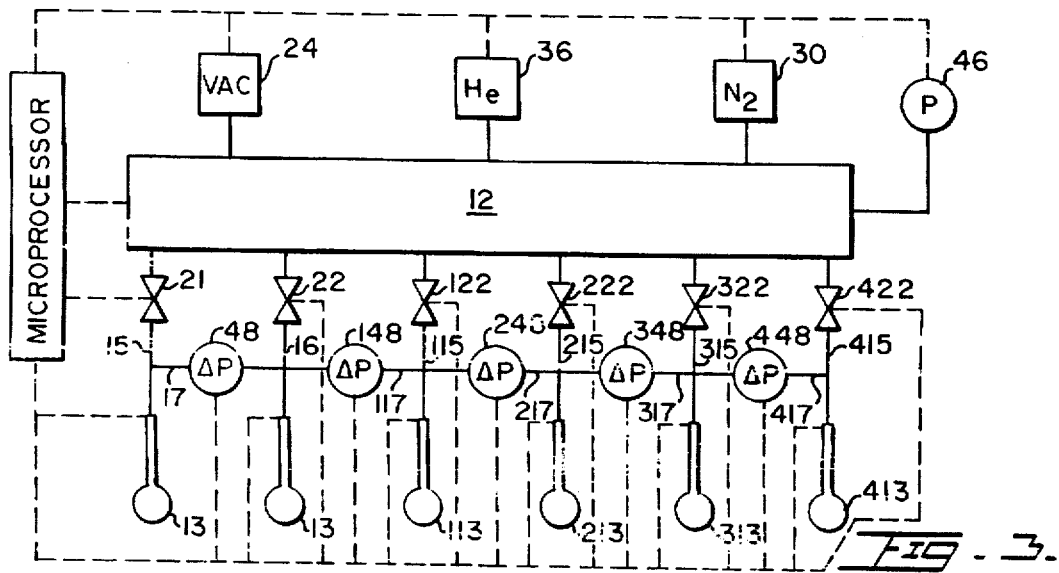
FIG. 3 is a schematic diagram of still another embodiment comprising a single manifold and six valved supply lines each coupled to a different one of six sample cells constructed and arranged in a manner similar to the arrangement of the sample cells of the FIG. 1 and FIG. 2 embodiments, wherein any one of said six cells can be selected as a reference cell.

It is suggested that the system of FIG. 2 be subjected to the leak test and that the system pass the leak test before further analysis is performed. In order to appreciate the analysis performed on the FIG. 2 embodiments a brief description of the FIG. 2 embodiment follows.

The embodiment of FIG. 2 is similar to that of FIG. 1 in that it includes all the elements of the FIG. 1 embodiment, and, in addition, is also provided with a third cell 113 (similar to cells 13 of the first embodiment), a third supply line 115 similar to supply lines 15 and 16 of the first embodiment and having a third isolation valve 122 (similar to isolation valves 21 and 22 of the first embodiment) and a second coupling line 117 (similar to coupling line 17) having a second differential pressure transducer or gauge 148 (similar to differential pressure transducer or gauge 48 of the first embodiment) coupling supply line 16 with third supply line 115.

The third cell 113 of the FIG. 2 embodiment is paired and compared with one of the cells 13 of the FIG. 2 embodiment, using a program similar to that used for the FIG. 1 analyzer, except for the fact that in comparing cell 113 with one of the cells 13 (for example, the cell at the distal end of supply line 16 provided with isolation valve 22), the comparison is made with isolation valve 21 closed throughout the comparison to isolate supply line 15 and using supply line 16 with isolation valve 22, second coupling line 117 with second differential pressure transducer or gauge 148 (similar to differential pressure transducer or gauge 48 of the FIG. 1 embodiment). The FIG. 2 embodiment can perform the method just described for the FIG. 1 embodiment, and after the data obtained from the comparison of the left and right cells 13, similar to those of FIG. 1, are stored, third cell 113 is compared with one of the cells 13.

In this comparison of third cell 113 with one of the previously compared cells 13, the method steps employed in the second analysis includes third supply line 115 with its isolation valve 122 instead of either supply line 15 and its isolation valve 21 or supply line 16 with its isolation valve 22 and second coupling line 117 with differential pressure transducer or gauge 148 instead of coupling line 17 with differential pressure transducer or gauge 48 and supply line 16 with isolation valve 22 or supply line 15 with isolation valve 21 and coupling line 17 (with its differential pressure transducer or gauge 48) and coupling line 117 (with its differential pressure transducer or gauge 148). Thus, cell 113 may be compared with either the cell that is analogous to the right cell 13 of the FIG. 1 analyzer or the cell that is analogous to the left cell 13 of the FIG. 1 analyzers The FIG. 2 embodiment contains all the elements of the FIG. 1 embodiment and, in addition, has an additional supply line 115 feeding additional cell 113 from manifold 12. An isolation valve 122 in line 115 has a function duplicating the function of isolation valve 22 in the FIG. 1 embodiment. Additional cell 113 serves as a second sample cell and its characteristics are compared with reference cell 13. A second coupling line 117 has a function and construction similar to those of coupling line 17 of the first embodiment, and to accomplish its objectives is coupled between supply line 115 and supply line 16 for the cell chosen by the processor to be the reference cell 13 for the second pair of comparison cells that includes additional cell 113 as its sample cell.

In using the FIG. 2 analyzer to compare cell 113 with the cell analogous with the right cell 13 of the FIG. 1 analyzer, isolation valve 21 remains closed throughout the comparison so that only supply lines 16 and 115 are subject to a program of opening and closing isolation valves 22 and 122 to control the flow of gas or vapor under pressure to dose either right cell 13 or cell 113 during their comparison. However, when cell 113 is compared with left cell 13, isolation valve 22 remains closed during the comparison, and isolation valves 21 and 122 are subject to a program of opening and closing to selectively dose either left cell 13 or cell 113 during the comparison. In the latter case, supply lines 15 and 115 cooperate with coupling lines 17 and 117 which latter become an extended coupling line.

The embodiment of FIG. 3 includes all the elements of that of FIG. 2, and, in addition, contains a fourth supply line 215 connected through a third coupling line 217 (containing differential pressure transducer or gauge 248 similar to differential pressure transducers or gauge 48 and 148) to third supply line 115 and containing isolation valve 222, a fifth supply line 315 connected through a fourth coupling line 317 (containing differential pressure transducer or gauge 348 similar to differential pressure transducers gauges 48, 148, and 248) to fourth supply line 215 and having a fifth isolation valve 322, and a sixth supply line 415 connected through a fifth coupling line 417 (containing differential pressure transducer or gauge 448 similar to differential pressure transducers or gauge 48, 148, 248 and 348) to fifth supply line 315 and having a sixth isolation valve 422. Each additional supply line and its associated isolation valve, coupling line and differential pressure transducer or gauge in the FIG. 3 analyzer operates in a manner consistent with the manner of operation of the third supply line 115 of the FIG. 2 embodiment so that the cell associated with each additional supply line is compared with a cell that has been compared previously until all the comparisons have been made.

The FIG. 3 embodiment can be used to pair and compare from two to six cells. For example, if two isolation valves of the six present are closed throughout and analysis, only four cells will be analyzed. Let us assume that isolation valves 322 and 422 are permanently closed throughout the analysis and the pressure readings of the system needed to compare left cells 13 with cell 213 with isolation valves 22, 122 and 222 closed and 21 open so that absolute pressure transducer or gauge 46 reads 420 mm for left cell 13, −3 mm for differential pressure transducer or gauge 48, +5 mm for differential pressure transducer or gauge 148, and +3 mm for differential pressure transducer or gauge 248.

The pressure reading for cell 213 is 425 mm derived by applying the differential pressures reported by differential pressure transducer or gauge 48 (−3 mm), differential pressure transducer 148 (+5 mm) and differential pressure transducer or gauge 248 (+3 mm), (which calculates to a net pressure differential of +5 mm) to the pressure reading for left cell 16 (420 mm). If an error of 1% is assumed for each differential pressure transducer or gauge, the error developed between left cell 13 and cell 213, which involves differential pressure readings from three differential pressure transducers or gauges 48, 148 and 248, each having a range of 10 mm in differential pressure readings, cannot exceed 3% with an RMS (root mean square) error of only 17%, or 0.3 mM. This yields a precision vastly improved over the 10 mm resolution obtainable from an absolute pressure transducer or gauge having a 1% accuracy over a pressure range of 1000 mm.

The FIG. 1 embodiment using a differential pressure transducer or gauge having a 1% accuracy over a 10 mm range of pressure readings (−5 mm to +5 mm) is the most accurate embodiment of this invention with a resolution of 0.1 mm pressure. The FIG. 3 embodiment and the FIG. 2 embodiment also have the same resolution as the FIG. 1 embodiment when only one differential pressure transducer or gauge is needed to compare the cells. However, even in its least precise application, the FIG. 3 embodiment has a maximum possible resolution of 0.5 mm when all five differential pressure transducers or gauges are needed to analyze two cells in the six cell system of the FIG. 3 embodiment, each differential pressure transducer or gauges having 1% accuracy. These resolutions obtainable by the embodiments described herein are all significantly less than the 10 mm resolution obtainable from the absolute pressure transducers or gauges having a 1% accuracy over a range of 1000 mm in pressure readings.

The present invention provides more accurate determinations of the data sought by analysis by using the combination of a differential pressure transducer or gauge with an absolute pressure transducer to determine the data for two sample cells substantially simultaneously instead of needing two absolute pressure transducers or gauges to determine the parameters of the two samples. The time for completing an analysis of a plurality of samples has been reduced between 5% and 95% of the time previously needed, because dosing of a cell whose pressure is determined to be less than the pressure of the other sample undergoing study can be equalized more readily by using a plurality of small doses monitored by a differential pressure transducer or gauge having a relatively large scale covering a relatively narrow range of pressures.

In accordance with the provisions of the patent statutes, applicant has provided a description of his invention with special emphasis on preferred embodiments thereof. It is understood that various modifications may be made within the scope of the claimed subject matter that follows without departing from the gist of this invention.

What is claimed:

1. An analyzer capable of performing adsorption and/or desorption analyses on samples comprising:
   a) a manifold,
   b) an absolute pressure transducer or absolute pressure gauge to monitor the pressure within said manifold,
   c) at least two cells comprising a pair of cells constructed and arranged to store a sample for analysis,
   d) a supply line interconnecting each of said cells to said manifold,
   e) an isolation valve in each of said supply lines between its interconnected cell and said manifold,
   f) a microprocessor constructed and arranged to select one of said cells as a reference cell and another of said cells as a sample cell when both said cells are provided with samples, and
   g) a differential pressure transducer or gauge between said cells below the isolation valves.

2. An analyzer as set forth in claim 1, wherein said differential pressure transducer or gauge is located between a first of said supply lines between its said isolation valve and its said cell connected thereto and to another of said supply lines between its said isolation valve and its said cell connected thereto, said microprocessor being constructed and arranged to correlate the opening and closing of said isolation valves with the application of gas or vapor from said manifold to one or the other of said cells, to monitor the pressure of said gas or vapor supplied to said one or said other cell, to compare the attained pressure in said cell with a first target pressure, to correlate the opening and closing of said isolation valves with the application of said gas or vapor from said manifold to the other of said cells, to select a second target pressure closer to the attained pressure in said one cell and obtain an attained pressure in both said cells of a pressure approximately said second target pressure in both of said cells without requiring an additional absolute pressure transducer or gauge to monitor either of said supply lines.

3. In an analyzer as set forth in claim 1, for use in adsorption analysis, said microprocessor including means for determining whether one cell or the other cell of said pair of cells has less pressure, dosing said cell whose pressure is less than said other cell of said pair of cells by an amount of pressure increase applied in one or more doses.

4. An analyzer as set forth in claim 1 wherein the number of differential pressure transducers included to measure the characteristics of said samples in said pair of said cells is less than the number of cells in said analyzer.

5. An analyzer for performing adsorption and/or desorption analyses on samples having elements comprising:
   a) a manifold,
   b) means to evacuate said manifold,
   c) means to store gas or vapor within said manifold,
   d) an absolute pressure transducer or absolute pressure gauge to monitor the pressure within said manifold,
   e) a first cell and a second cell comprising a pair of cells, each of said cells being constructed and arranged to store a powder sample for analysis,
   f) separate supply lines constructed and arranged to couple said first cell and said second cell with said manifold,
   g) an isolation valve in each of said supply lines constructed and arranged to isolate its associated cell from said manifold when said isolation valve is closed and to allow communication of gas or vapor between said associated cell and said manifold when said isolation valve is open,
   h) a coupling line connecting said supply lines between said isolation valves and said cells,
   i) a differential pressure transducer or differential pressure gauge in said coupling line constructed and arranged to measure a pressure differential, if any, between said cells when each of said cells has a powder sample and,
   j) a microprocessor constructed and arranged to actuate said means to evacuate said manifold, to store said gas or vapor in said manifold, to control the opening and closing of said isolation valves according to a predetermined cycle of steps, and to monitor said differential pressure transducer or differential pressure gauge.

6. An analyzer as set forth in claim 5, wherein said differential pressure transducer or differential pressure gauge operates over a smaller pressure range than the pressure range of the pressure monitoring means for said manifold.

7. An analyzer as set forth in claim 5, wherein said differential pressure transducer or differential pressure gauge operates over a pressure range at most equal to the pressure range of the pressure monitoring means for said manifold.

8. An analyzer as set forth in claim 5, further including additional elements comprising a third supply line having an isolation valve, and an additional coupling line having an additional differential pressure transducer or differential pressure gauge connecting said third supply line with at least one of said first named pair of supply lines, said microprocessor being constructed and arranged to control the operation of said additional elements associated with said third supply line.

9. An analyzer as set forth in claim 8, further including more additional elements comprising at least one more additional supply line constructed and arranged as a fourth supply line, at least one more additional coupling line constructed and arranged to couple said at least one more additional supply line to said fourth supply line, said microprocessor being also constructed and arranged to control the operation of the additional elements associated with said at least one more additional supply line.

10. An analyzer as set forth in claim 5, wherein the number of differential pressure transducers included to measure the characteristics of said samples in said pair of said cells is one less than the number of cells in said analyzer.

11. An analyzer as set forth in claim 5, wherein said microprocessor is constructed and arranged to open one of said isolation valves in the supply line feeding said one of said cells of said pair of cells when the latter initially indicates said one of said cells has a lower pressure than the other of said pair of cells and to close another isolation valve in the supply line feeding said other cell of said pair of cells that initially indicates a higher pressure for said other cell of said pair of cells.

12. An analyzer as set forth in claim 11, wherein said microprocessor is constructed and arranged to control the closing of both of said isolation valves when the pressure difference indicated for said cells in said pair of cells falls to an acceptable tolerance.

13. An analyzer as set forth in claim 11, wherein said microprocessor is constructed and arranged to close the open isolation valve and open the closed isolation valve if the differential pressure transducer or differential pressure gauge indicates that the cell initially at higher pressure now has a pressure different from that of the other cell of said pair of cells by a pressure differential greater than an acceptable tolerance.

14. A method of measuring the pressure of a pair of sample cells having a sample in each said cell comprising using a sample analyzer having a manifold, an absolute pressure transducer to measure the pressure in said manifold, a pair of supply lines extending from said manifold, a cell at the distal end of each of said supply lines, an isolation valve in each of said supply lines and a differential pressure transducer connected between said pair of supply lines between said isolation valves and said cells, selecting one of said cells to be a sample cell and the other of said cells to be a reference cell, closing the isolation valve associated with said sample cell, opening the isolation valve associated with said reference cell, measuring the pressure in said sample cell by summing the pressure measurement of said absolute pressure transducer and the pressure measurement of said differential pressure transducer.

15. A method for use in measuring the pressure of more than two sample cells comprising selecting more than two sample cells, performing the method of claim 12 on a pair of said cells taken from said more than two sample cells, followed by performing the method of claim 12 on a different pair of sample cells, at least one of said latter different pair not included in said first pair, to measure the pressure of said latter different pair of sample cells.

16. A method of performing adsorption and/or desorption analyses on powder samples comprising using a sample analyzer having a manifold, a pair of supply lines extending from said manifold, a cell at the distal end of each of said supply lines, a pair of isolation valves comprising an isolation valve in each of said supply lines and a differential pressure transducer or gauge connected between said pair of supply lines between its said isolation valve and its said cell associated with one of said pair of supply lines and said isolation valve and said cell associated with the other of said pair of supply lines, said differential pressure transducer or gauge having a smaller range than the range of an absolute pressure transducer or gauge associated with said manifold to monitor the pressure in said manifold, applying a powder sample to each of said cells, evacuating said manifold while both of said isolation valves are closed, increasing the pressure in the manifold to a higher pressure sufficient to deliver a dose of gas or vapor that will achieve a pressure in a desired pressure range in one of said cells in a preselected limited time when said one of said pair of isolation valves associated with said one of said supply lines and with said one of said cells associated therewith is opened, allowing sufficient time for said gas or vapor to transfer into said one of said cells to produce a higher cell pressure within said one of said cells of said pair of cells closer to the cell pressure of the other of said pair of cells, closing said one isolation valve, calculating the volume of gas or vapor added to said one cell by determining the change in pressure in the manifold before and after said gas or vapor transfer, determining which of said cells of said pair of cells has a higher cell pressure after said gas or vapor transfer, opening one or the other isolation valve of said pair of isolation valves that controls the flow of gas or vapor into an appropriate cell from said pair of cells that has a lower cell pressure after the aforesaid gas or vapor transfer, closing said one isolation valve controlling the gas or vapor transfer into said cell having a lower cell pressure that is closer to the pressure of the cell having a higher cell pressure after said gas or vapor transfer by appropriately opening and closing the isolation valves of said pair of isolation valves and repeating closing steps to said pair of cells until the difference in pressure between said cells, is within said acceptable tolerance.

17. A method as set forth in claim 14, for use with an analyzer having more than two cells, each cell with a separate associated supply line, and a separate isolation valve and a coupling line, each of said coupling lines provided with a differential pressure transducer or gauge and constructed and arranged for interconnection between any two of said coupling lines having the construction and arrangement of the differential pressure transducer of claim 14, comprising newly selecting a cell other than one of the two cells compared in the analysis of claim 14, pairing said newly selected cell with one of the two cells previously compared in the test of claim 14 to form a second pair of cells for comparison, closing every isolation valve controlling the flow of gas or fluid from the manifold to any cell other than the second pair of cells selected for comparison and performing an analysis of said second pair of cells following the steps performed in the analysis of claim 14 while the isolation valves controlling the flow of gas or vapor between said manifold and any of said cells not selected for said second pair of cells for comparison remain closed throughout said analysis of said second pair.

\* \* \* \* \*